(12) United States Patent
Wasielewski (10) Patent No.: US 7,309,361 B2
(45) Date of Patent: Dec. 18, 2007

(54) BIOLOGIC MODULAR TIBIAL AND FEMORAL COMPONENT AUGMENTS FOR USE WITH TOTAL KNEE ARTHROPLASTY

(76) Inventor: Ray C. Wasielewski, 7590 Brandon Rd., New Albany, OH (US) 43054

( * ) Notice: Subject to any disclaimer, the term of this patent is extended or adjusted under 35 U.S.C. 154(b) by 489 days.

(21) Appl. No.: 10/612,079

(22) Filed: Jul. 2, 2003

(65) Prior Publication Data

US 2004/0083003 A1    Apr. 29, 2004

Related U.S. Application Data

(60) Provisional application No. 60/420,567, filed on Oct. 23, 2002.

(51) Int. Cl.
*A61F 2/38* (2006.01)
(52) U.S. Cl. .................................. 623/20.14
(58) Field of Classification Search ............. 623/16.11, 623/18.11, 20.14, 20.15, 20.16, 20.17, 20.19, 623/20.21, 20.26–20.28, 20.3, 20.31, 20.32, 623/23.39, 23.57, 23.58, 23.59, 22.37, 22.4–22.46, 623/20.24
See application file for complete search history.

(56) References Cited

U.S. PATENT DOCUMENTS

| | | | |
|---|---|---|---|
| RE29,757 E | * | 9/1978 | Helfet ........................ 623/20.31 |
| 4,790,853 A | * | 12/1988 | Engelbrecht et al. ..... 623/20.25 |
| 4,990,161 A | * | 2/1991 | Kampner .................. 623/18.11 |
| 5,007,933 A | | 4/1991 | Sidebotham et al. |
| 5,147,405 A | | 9/1992 | Van Zile et al. |
| 5,282,869 A | | 2/1994 | Miyajima et al. |
| 5,330,532 A | | 7/1994 | Ranawat |
| 5,344,654 A | * | 9/1994 | Rueger et al. .............. 424/423 |
| 5,458,653 A | * | 10/1995 | Davidson .................. 623/23.36 |
| 5,522,895 A | | 6/1996 | Mikos |
| 5,556,433 A | | 9/1996 | Gabriel et al. |
| 5,571,193 A | * | 11/1996 | Kampner .................. 623/23.57 |
| 5,759,205 A | * | 6/1998 | Valentini ..................... 433/173 |
| 5,824,102 A | | 10/1998 | Buscayret |
| 5,876,446 A | * | 3/1999 | Agrawal et al. ......... 623/23.61 |
| 6,056,777 A | | 5/2000 | McDowell |

(Continued)

FOREIGN PATENT DOCUMENTS

DE    197 16 051 A1    11/1997

(Continued)

*Primary Examiner*—Anuradha Ramana
(74) *Attorney, Agent, or Firm*—Taft Stettinius & Hollister LLP (57) ABSTRACT

The use of biologic and/or biologically reabsorbable materials to provide temporary stability after a surgical joint procedure is provided. Exemplary embodiments of the invention provide biologic and/or biologically reabsorbable cam and/or post linings mounted to respective knee prosthesis components. Such linings are reabsorbed after a time sufficient for patient tissue formation to provide permanent stability. Likewise, the invention has application in any joint reconstruction where the integrity of the stabilizing tissue has been compromised by injury or as a result of the surgical procedure itself. Further aspects of the present invention include using biologic and/or biologically reabsorbable materials loaded with agents that may promote tissue formation, fight infection, and promote clotting. Still further aspects of the present invention are directed to the use of biologically reabsorbable snaps or other fasteners to attach a lining to the femoral component and/or the tibial component.

36 Claims, 8 Drawing Sheets

U.S. PATENT DOCUMENTS

| | | | |
|---|---|---|---|
| 6,110,482 A * | 8/2000 | Khouri et al. | 424/423 |
| 6,113,640 A | 9/2000 | Tormala et al. | |
| 6,136,029 A * | 10/2000 | Johnson et al. | 623/16.11 |
| 6,171,340 B1 | 1/2001 | McDowell | |
| 6,203,573 B1 | 3/2001 | Walter et al. | |
| 6,261,586 B1 * | 7/2001 | McKay | 424/423 |
| 6,264,697 B1 | 7/2001 | Walker | |
| 6,281,262 B1 | 8/2001 | Shikinami | |
| 6,325,828 B1 | 12/2001 | Dennis et al. | |
| 6,406,498 B1 | 6/2002 | Tormala et al. | |
| 6,461,320 B1 * | 10/2002 | Yencho et al. | 604/8 |
| 6,527,810 B2 * | 3/2003 | Johnson et al. | 623/23.56 |
| 6,592,622 B1 * | 7/2003 | Ferguson | 623/13.14 |
| 6,616,698 B2 * | 9/2003 | Scarborough | 623/23.51 |
| 6,652,587 B2 * | 11/2003 | Felt et al. | 623/20.16 |
| 6,746,773 B2 * | 6/2004 | Llanos et al. | 428/421 |
| 2001/0020188 A1 | 9/2001 | Sander | |
| 2001/0039455 A1 * | 11/2001 | Simon et al. | 623/23.51 |
| 2002/0173852 A1 * | 11/2002 | Felt et al. | 623/20.32 |
| 2003/0023316 A1 | 1/2003 | Brown et al. | |

FOREIGN PATENT DOCUMENTS

| | | |
|---|---|---|
| EP | 1201204 A2 | 5/2002 |
| EP | 03 776 470.1 | 6/2007 |
| WO | WO 97/14447 | 4/1997 |

* cited by examiner

BIOLOGIC MODULAR TIBIAL AND FEMORAL COMPONENT AUGMENTS FOR USE WITH TOTAL KNEE ARTHROPLASTY

REFERENCE TO RELATED APPLICATION

This application claims the benefit of U.S. Provisional Application Ser. No. 60/420,567, entitled "BIOLOGIC MODULAR TIBIAL AND FEMORAL COMPONENT AUGMENTS FOR USE WITH TOTAL KNEE ARTHROPLASTY", filed on Oct. 23, 2002, the disclosure of which is incorporated herein by reference.

BACKGROUND

1. Field of the Invention

The present invention is directed toward stabilizing components for use with joints of the body. Examples of such joints include hip joints, shoulder joints, elbow joints, ankle joints, and knee joints. More specifically, aspects of the present invention are directed toward biologic and biologically reabsorbable stabilizing components to at least temporarily augment a knee prosthesis to provide a level of medial, and/or later, and/or anterior, and/or posterior, and/or subluxation stability proportional to patient recover time in response to a total knee arthroplasty procedure to bridge any deficiency in stability that is a resultant of the surgerical procedure.

2. Background of the Invention

A human knee joint consists of the articulation between the femur and the tibia. The femur includes a lateral condyle and a medial condyle riding upon the lateral meniscus and the medial meniscus on the tibial plateau. An intercondylar channel is formed allowing throughput of the anterior cruciate ligament and the posterior cruciate ligament.

Total knee replacement surgery begins by making an incision exposing the knee joint. The femur is separated from the tibia and the damaged portions of the femur are removed. During this procedure various ligaments are impaired or removed, potentially decreasing the medial, lateral, anterior, posterior, and/or suxluxation stability. The removal of the damaged portions leaves the femur contoured to accept a femoral prosthetic component cemented thereto. Likewise, the tibia is manipulated to remove the damaged bone and tissue, leaving a contoured aspect to receive the tibial prosthetic component cemented thereto.

Figure 1:
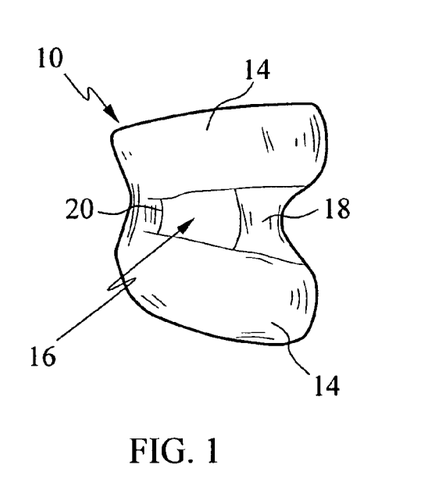
FIG. 1 is a perspective view, from below, of a prior art prosthetic femoral component for use in total knee replacement surgery.
Figure 2:
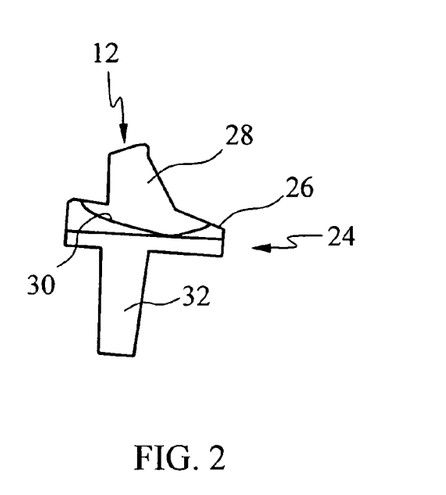
FIG. 2 is a perspective view, from the side, of a prior art prosthetic tibial component for use in total knee replacement surgery.
Figure 3:
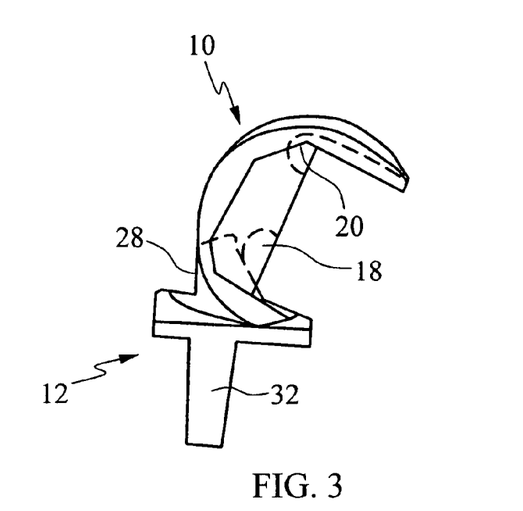
FIG. 3 is a perspective view, from the side, of the interaction between the prior art prosthetic femoral component and the prior art prosthetic tibial component according to an angle less than 90° between femur and tibia.
Figure 4:
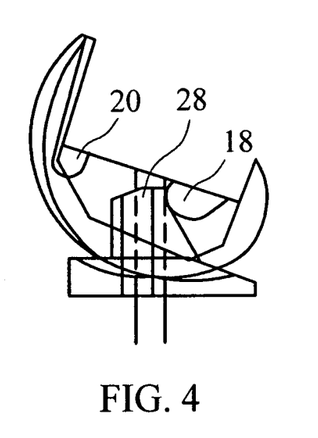
FIG. 4 is a perspective view, from the side, of the interaction between the prior art prosthetic femoral component and the prior art prosthetic tibial component according to an angle less than 145° between femur and tibia.
Figure 5:
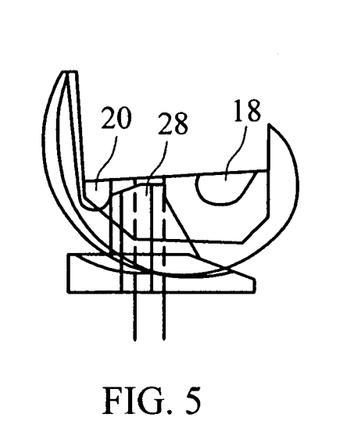
FIG. 5 is a perspective view, from the side, of the interaction between the prior art prosthetic femoral component and the prior art prosthetic tibial component according to an angle of approximately 180° between femur and tibia.

FIGS. 1-5 illustrate a prior art knee replacement prosthesis that includes a femoral component 10 (see FIG. 1) and a tibial component 12 (see FIG. 2), and the interaction therebetween (see FIGS. 3-5).

The femoral component 10, adapted to be implanted on the distal end of the patient's femur, includes a pair of convex bearing surfaces 14 that are separated by an intercondylar channel 16. Provided within the intercondylar channel 16 is a posterior cam 18 and an anterior cam 20.

The tibial component 12, adapted to be implanted on the proximal end of the patient's tibia, includes a tibial insert 24 and an upper aspect 26 exhibiting a stabilizing post 28 and a pair of concave bearing surfaces 30 that receive the convex bearing surfaces 14 of the femoral component. The tibial insert 24 also includes a distal stem portion 32 for mounting the tibial component 12 to the tibia.

As the knee flexes, the femur (see FIG. 5) rotates clockwise relative to the tibial component 12. This brings the posterior cam 18 into contact with the stabilizing spine 28. This interaction prevents anterior translation of the femur relative to the tibial component 12 as the spine 28 blocks this motion. With further flexion, the interaction of the tibial insert spine 28 with the posterior cam 18 forces posterior translation of the femoral component 10 relative to the tibia (rollback). This rollback allows for optimal knee flexion.

As the knee extends beyond neutral (see FIG. 5), the anterior femoral component cam prevents counterclockwise motion of the femoral component relative to the tibia. This interaction prevents pyperextension of the knee joint.

Stability after total knee arthroplasty is a pressing problem in primary and revision total knee arthorplasty. Ligament stability can be lost from over-release of the medial collateral ligament during balancing. The ligaments about the knee are often deficient as a result of as a result of removal or damaged caused during the total knee arthroplasty procedure itself. These deficient ligaments could be reconstructed using biologic ligaments but these would need temporary support as they become competent. While a VVC (Varus/Valgus Constraining) total knee arthroplasty with permanent cam post mechanism could be utilized, long term this constraint could result in losing at the other interfaces.

SUMMARY OF THE INVENTION

The invention is directed toward use of biologic and/or biologically reabsorbable materials to provide temporary stability after a surgical joint procedure. Exemplary embodiments of the invention provide biologic and/or biologically reabsorbable cam and/or post augments (i.e. linings & caps) mounted to respective knee prosthesis components. Such biologic and/or biologically reabsorbable augments are reabsorbed after a time sufficient for patient tissue formation to provide permanent stability. As these augments are absorbed, any biologic debris would not be considered third body particulate as, for example, PLLA and SIS are not more rigid than any of the prosthesis components. Likewise, the invention has application in any joint reconstruction where the integrity of the stabilizing tissue has been compromised by injury or as a result of the surgical procedure itself. Further aspects of the present invention are directed toward using biologic and/or biologically reabsorbable materials loaded with agents that may promote tissue formation, fight infection, and promote clotting. Still further aspects of the present invention are directed to the use of biologically reabsorbable snaps or other fasteners to attach an augment to the femoral component and/or the tibial component.

Particular embodiments make use of stabilizing augments adapted to be mounted to the stabilizing post of a tibial component and/or the intercondylar channel of the femoral component to concurrently provide periarticular stability and the range of motion desired by patients after surgery, but with the additional benefit of doing so without substantially increasing the risks of dislocation and additional surgery to repair the dislocation. At least one of the exemplary embodiments utilizes a biologically reabsorbable material to temporarily provide such periarticular stability, allowing the physician to manipulate the stabilizing device to match the contour of the particular tibial and femoral prosthetic components selected as well as providing additional material if greater stabilization is deemed appropriate. In such an embodiment, it is envisioned that the biologically reabsorbable material degrades in general proportion to the level of tissue developed by the patient's own body to supplement periarticular stability of the knee joint. Thus, the artificial stabilizing device may degrade inversely proportional to the patient's need for artificial stabilization.

It is a first aspect of the present invention to provide a prosthetic stabilizing device for use with a knee replacement prosthesis, which includes a tibial component adapted to be mounted to a patient's tibia and a femoral component adapted to be mounted to the patient's femur, and where the tibial component interfaces with the femoral component to simulate the biomechanics of a knee joint. The stabilizing device includes: (a) a lining adapted to be mounted to a tibial component of a knee replacement prosthesis and/or a femoral component of the knee replacement prosthesis so that the lining is positioned between the tibial component and the femoral component approximate a prosthetic intercondylar channel of the femoral component to supplement periarticular stability between the tibial component and the femoral component; and (b) where the lining is comprised of a lining material that is or includes a biologic material, a biologically reabsorbable material, and/or a combination of biologic and biologically reabsorbable materials.

It is a second aspect of the present invention to provide a prosthetic stabilizing device for use with a knee replacement prosthesis, which includes a tibial component adapted to be mounted to a patient's tibia and a femoral component adapted to be mounted to the patient's femur, and where the tibial component interfaces with the femoral component to simulate the biomechanics of a knee joint. The stabilizing device includes: (a) a first lining adapted to be mounted to a tibial component and/or a femoral component so that the first lining is positioned between the tibial component and the femoral component approximate a prosthetic intercondylar channel to supplement periarticular stability between the tibial component and the femoral component; and (b) a second lining adapted to be mounted to at least the other component so that the second lining is positioned between the tibial component and the femoral component approximate the prosthetic intercondylar channel to supplement periarticular stability of the tibial component and the femoral component; where the first lining is comprised of a first lining material that is a biologic material, a biologically reabsorbable material, or a combination of biologic and biologically reabsorbable materials; and where the second lining is comprised of a second lining material that is or includes a biologic material, a biologically reabsorbable material, or a combination of biologic and biologically reabsorbable materials.

It is a third aspect of the present invention to provide a knee prosthesis that includes: (a) a tibial component adapted to be mounted to a patient's tibia; (b) a femoral component adapted to be mounted to a patient's femur, and to be pivotally coupled to the tibial component to form a prosthetic knee joint; and (c) a lining adapted to be mounted to the tibial component and/or the femoral component in the prosthetic knee joint so that the lining is positioned between the tibial component and the femoral component approximate a prosthetic intercondylar channel of the femoral component to supplement periarticular stability between the tibial component and the femoral component; and where the lining is comprised of a lining material that is or includes a biologic material, a biologically reabsorbable material, or a combination of biologic and biologically reabsorbable materials.

It is a fourth aspect of the present invention to provide a knee prosthesis that includes: (a) a femoral component adapted to be mounted to a patient's femur; (b) a tibial component adapted to be mounted to the patient's tibia, where the tibial component includes a stabilizing post at its proximal end adapted to be received within a prosthetic intercondylar channel of the femoral component to form a prosthetic hinge-type joint coupling; and (c) a lining mounted to the stabilizing post and/or an inner surface of the femoral component at least partially defining the prosthetic intercondylar channel, to, at least temporarily, supplement periarticular stability between the stabilizing post and the prosthetic intercondylar channel; wherein the lining is comprised of a lining material that is or includes a biologic material, a biologically reabsorbable material, or a combination of biologic and biologically reabsorbable materials.

It is a fifth aspect of the present invention to provide a stabilizing device for use with a joint reconstruction surgical procedure that includes the interface between at least two bones exhibiting biomechanics of a joint, where stabilizing device includes: (a) a lining adapted to be mounted to a first bone and/or a second bone so that the lining is positioned between an interface of the first bone and the second bone to assist in maintaining the stability and functionality of a joint formed at least in part by the interface of the first and second bone; and (b) the lining comprises a lining material that is or includes a biologic material, a biologically reabsorbable material, or a combination of biologic and biologically reabsorbable materials.

It is a sixth aspect of the present invention to provide a method for providing at least temporary stability to a prosthetic knee joint, which includes a tibial component interfacing a femoral component, where the tibial and femoral components simulate at least certain biomechanics of a knee joint. The method includes the step of mounting a stabilizing device to the femoral component and/or the tibial component to improve periarticular stability to the prosthetic knee joint, where the stabilizing device is comprised of a material that is or includes a biologic material, a biologically reabsorbable material, or a combination of biologic and biologically reabsorbable materials.

DESCRIPTION OF THE PRESENT INVENTION

The exemplary embodiments described herein relate to stabilizing devices and techniques for use in joint reconstruction and replacement surgery. The inventions described herein will be described with respect to knee reconstruction and total knee replacement, however, it should be understood that these exemplary applications do not limit the scope of the invention to such applications. Thus, it will become apparent to those of ordinary skill in the art that the devices and techniques disclosed herein may be useful for other types of implants and orthopedic surgeries; and, specifically, other joint prosthetics.

For the purposes of this disclosure, "biologic material" refers to material being derived or synthesized from living organisms, cell, tissues, and/or their products. A biologic material may or may not be a biologically reabsorbable material.

For the purposes of this disclosure, "biologically reabsorbable material" refers to material that is biologically compatible with the mammalian body having the capacity to degrade within, dissolve within, and/or be absorbed by the mammalian body. A biologically reabsorbable material may be a biologic material, a naturally occurring material, or a synthetic material.

Figure 6:
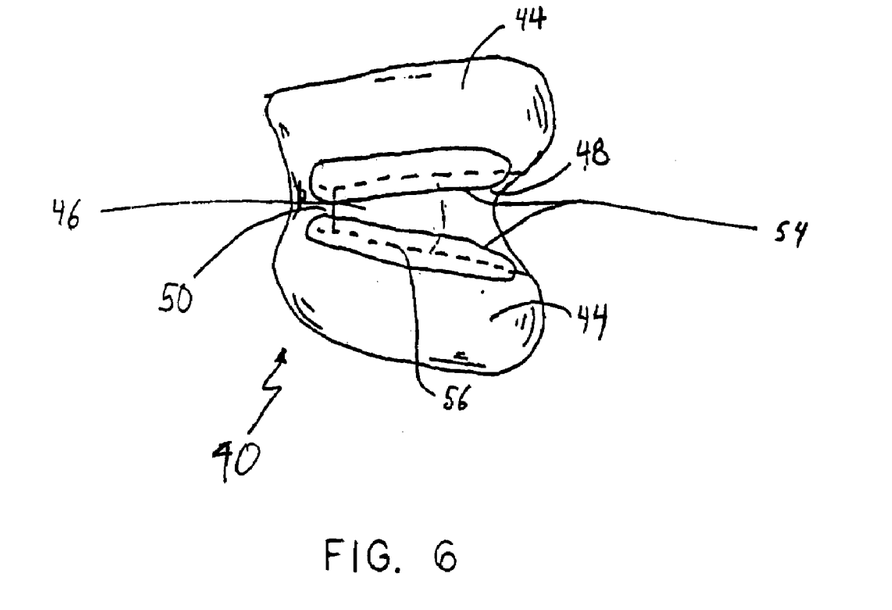
FIG. 6 is a perspective view, from below, of an exemplary embodiment of the present invention mounted to a femoral prosthesis component.
Figure 7:
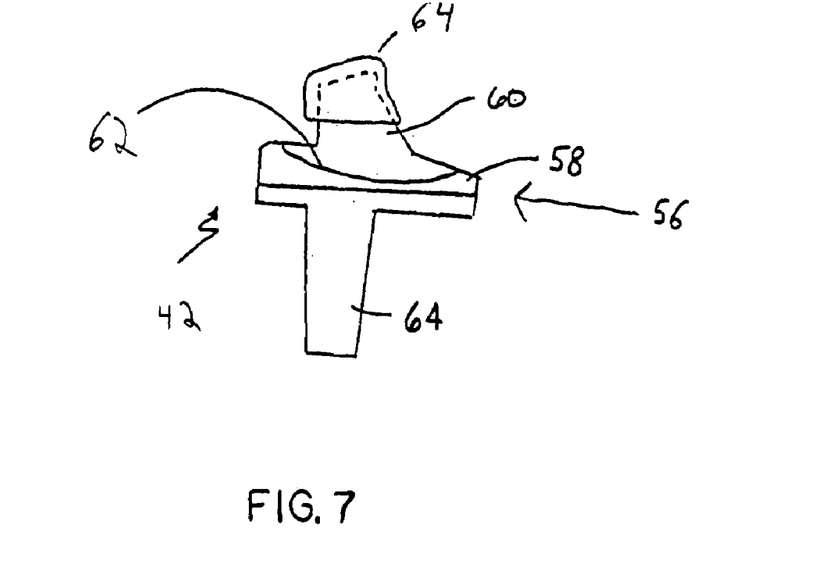
FIG. 7 is a perspective view, from the side, of another exemplary embodiment of the present invention mounted to a tibial prosthesis component.

As shown in FIGS. 6 and 7, exemplary embodiments of the present invention include a femoral component 40 and a tibial component 42 of a prosthetic knee joint manufactured or modified in accordance with certain aspects of the present invention. The femoral component 40 is adapted to be mounted or implanted to a distal end of a femur, while the tibial component 42 is adapted to be mounted or implanted to the proximal of a tibia during a total knee replacement procedure. As discussed above, the femoral component 40 and tibial component 42 are coupled together in a pivotal coupling to form a prosthetic knee joint.

Referencing FIG. 6, the femoral component 40 of an exemplary embodiment includes a pair of convex bearing surfaces 44 that are separated by an intercondylar channel 46. The intercondylar channel 46 is bounded by a posterior cam 48 and an anterior cam 50. Biologic and/or biologically reabsorbable liners 54 are mounted to the inner walls 56 of the intercondylar channel 46 of the femoral component 40 by way of a fastener such as a suture, suture anchor, adhesive, screw, rivet, or any other effective fastening mechanism or procedure.

Referencing FIG. 7, the tibial component 42 of another exemplary embodiment includes a tibial insert 56 having a distal stem portion 64 for mounting the tibial component 42 to the tibia, and an upper aspect 58 that includes a stabilizing post 60 and a pair of concave bearing surfaces 62 flanking the post 60 that receive the convex bearing surfaces of the femoral component 40 when coupled to the femoral component to form a knee joint. A biologic and/or biologically reabsorbable liner/cap 64 is mounted to the stabilizing post 60 utilizing any effective fastening mechanism or procedure.

Figure 8:
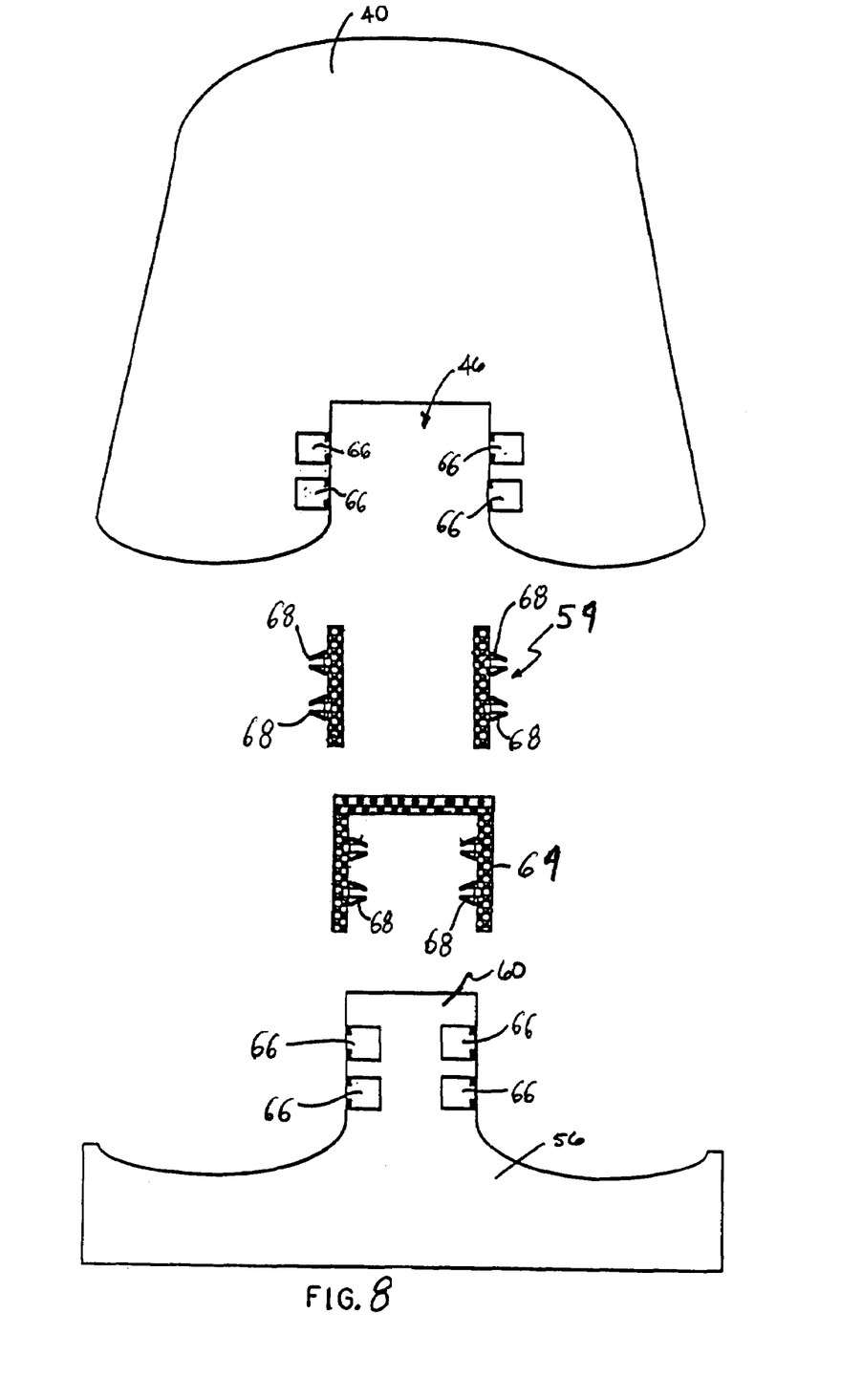
FIG. 8 is an exploded view of exemplary embodiments of the present invention mounted to a prosthetic knee.

As shown in FIG. 8, a physician in an exemplary procedure selects a femoral component 40 and a complementary tibial component 42 (shown as tibial insert 56 for simplicity) and prepares the respective bones for mounting or implanting the components thereto. Each of the components 40, 42 may come manufactured to include one or more biologic and/or biologically reabsorbable liners 54 and/or 64 previously mounted thereto, or include recesses 66 for accepting snap-fit fasteners 68 extending from the liners. Of course, alternate fasteners such as, without limitation, a suture, suture anchor, adhesive, screw, dowel, or rivet may also be used. Conversely, the components 40, 42 may have been manufactured without contemplation of biologic and/or biologically reabsorbable liners 54, 64 being mounted thereto. As such, the preparation may include, for example, adding recesses 66 to accept the fasteners 68 of the liners 54, 64. It will be appreciated that the liners may be attached prior to implanting the femoral and/or tibial components, or may be attached after implanting the femoral and/or tibial components. As a result of attaching the liners, when the prosthetic knee joint is initially implanted, there will initially be a substantial decrease in appreciable tolerance between the intercondylar channel 46 and the stabilizing post 60, which may result in increased periarticular stability.

As the patient's natural tissue forms and heals around the implanted prostheses, the biologic and/or biologically reabsorbable liners 54, 64 or inserts 70 (described below) may be selected to degrade, dissolve, or be absorbed by the patient's body over time to correspond with the reconstruction of the patient's natural tissue. Thus, as the biologic and/or biologically reabsorbable material is degrading, it is desired that the stability attributable to the amount of the liner(s) absorbed by the patient's body be substantially compensated by the patient's progressive level of natural tissue reconstruction. It is also desired that as the biologic and/or biologically reabsorbable material of the liner(s) is dissolved or consumed by the patient's body, the prosthetic knee joint may provide a less constrained gait for the patient and may better simulate the flexing of a natural knee in all three dimensions.

Figures 9, 10:
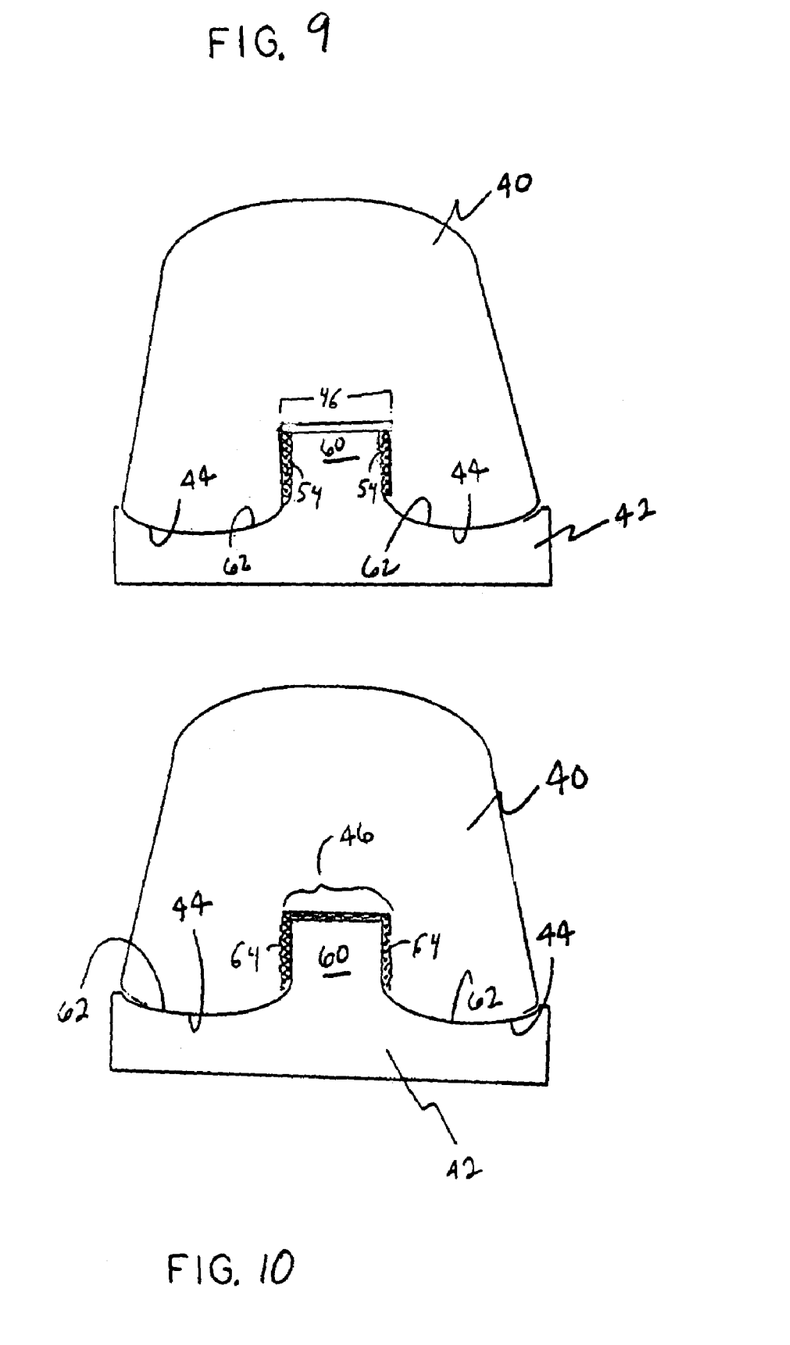
FIG. 9 is a frontal view showing the interaction between the tibial component and the femoral component having the exemplary embodiment of FIG. 6 mounted to the femoral prosthesis component.
FIG. 10 is a frontal view showing the interaction between the tibial component and the femoral component having the exemplary embodiment of FIG. 7 mounted to the tibial prosthesis component.
Figure 11:
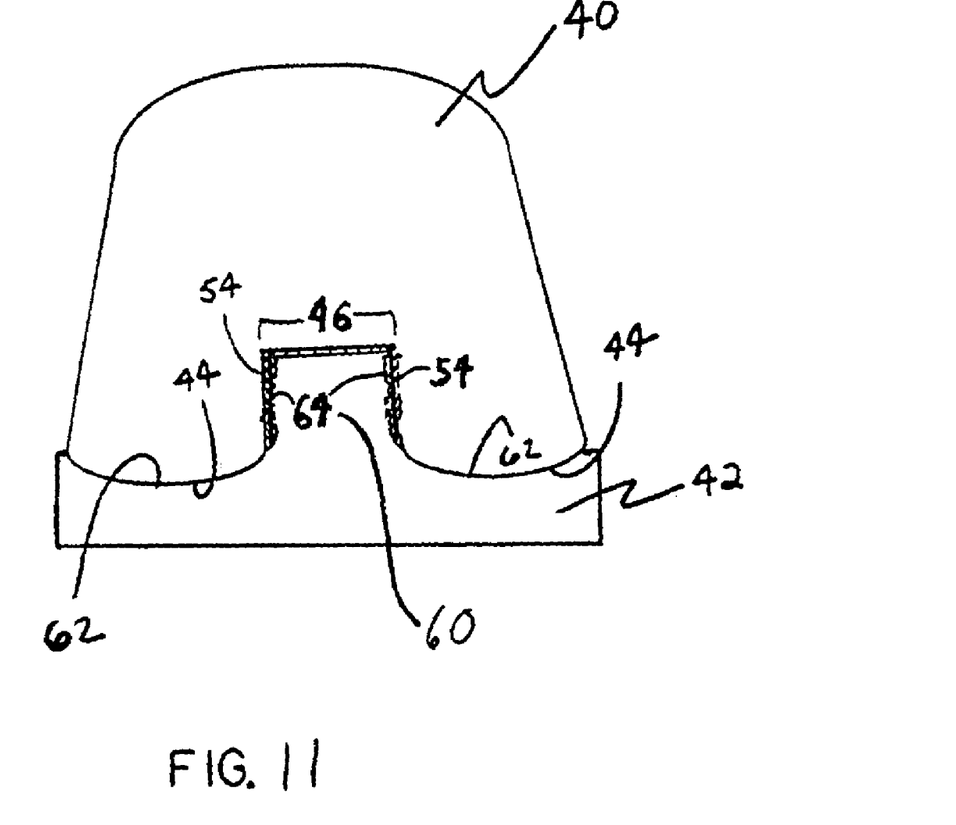
FIG. 11 is a frontal view showing the interaction between the tibial component and the femoral component concurrently having the exemplary embodiment of FIG. 6 mounted to the femoral prosthesis component and the exemplary embodiment of FIG. 7 mounted to the tibial prosthesis component.

FIG. 9 shows an example of the reduced space between the stabilizing post 60 and intercondylar channel 46 in accordance with an embodiment utilizing biologic and/or biologically reabsorbable liners 54 mounted in the intercondylar channel 46 of the femoral component 40. Also, FIG. 10 shows an example of the reduced space between the stabilizing post 60 and intercondylar channel 46 in accordance with an exemplary embodiment utilizing the biologic and/or biologically reabsorbable liner or cap 64 mounted only on the stabilizing post 60 of the tibial component 42. Likewise, FIG. 11 shows an example of the reduced space between the stabilizing post 60 and intercondylar channel 46 when liners 54 are mounted in the intercondylar channel 46 of the femoral component 40 and a liner/cap 64 is mounted to the stabilizing post 60 of the tibial component 42.

Figure 12:
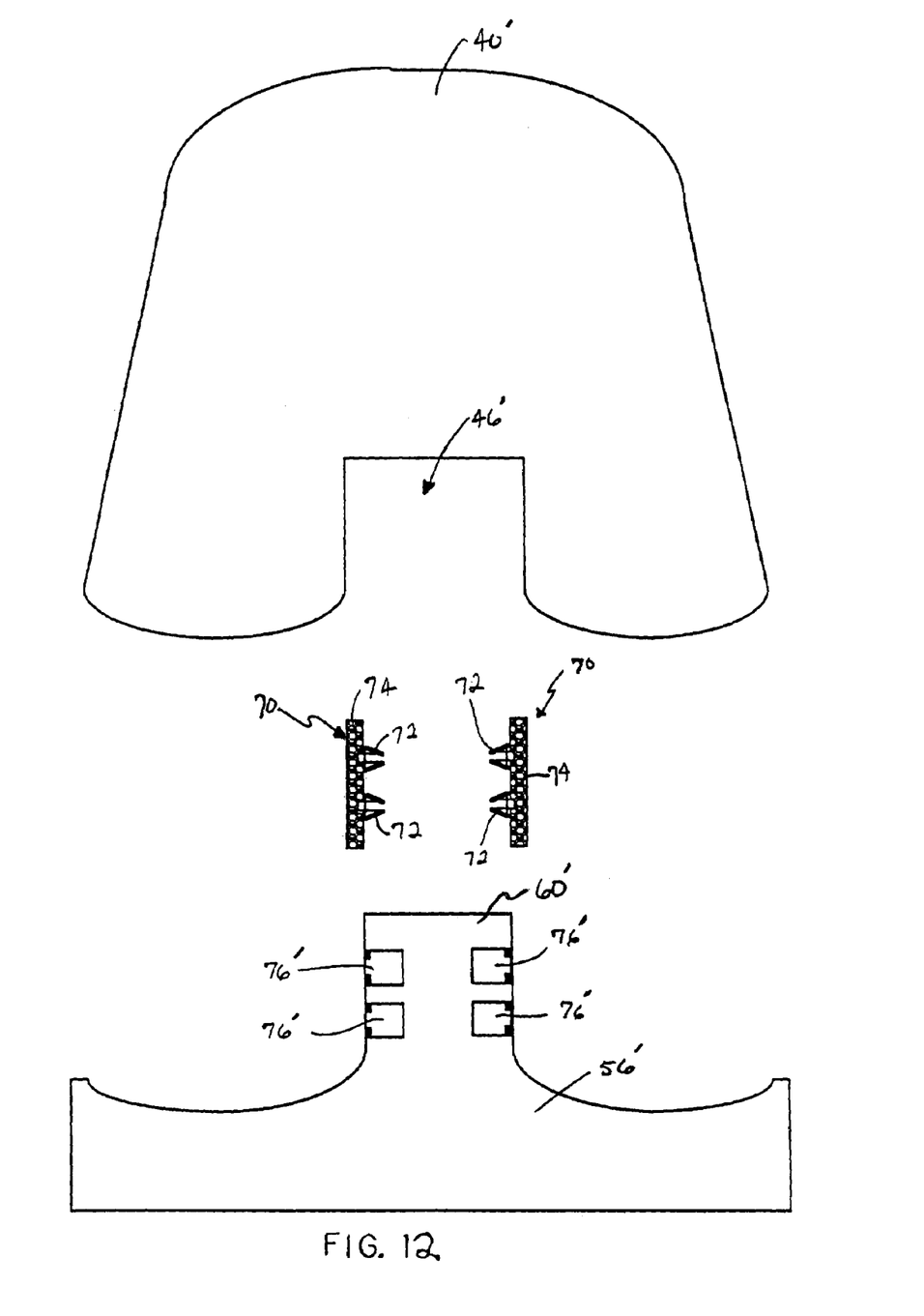
FIG. 12 is an exploded view of a knee prosthesis that includes exemplary another embodiment exhibiting fasteners for securing the embodiment to the tibial prosthesis component.
Figure 13:
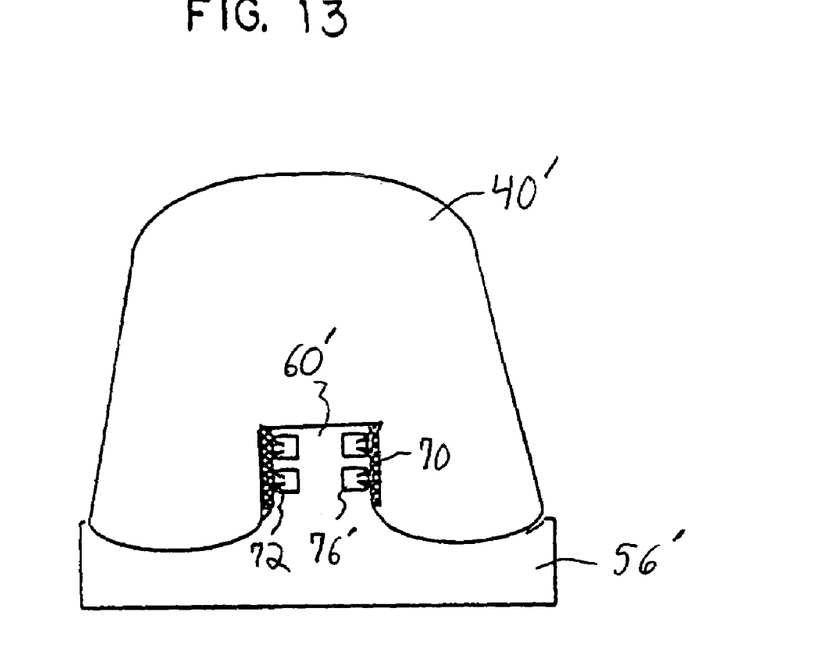
FIG. 13 is a frontal view showing the interaction between the tibial component and the femoral component concurrently having the exemplary embodiment of FIG. 12 mounted to the tibial component.
Figure 14:
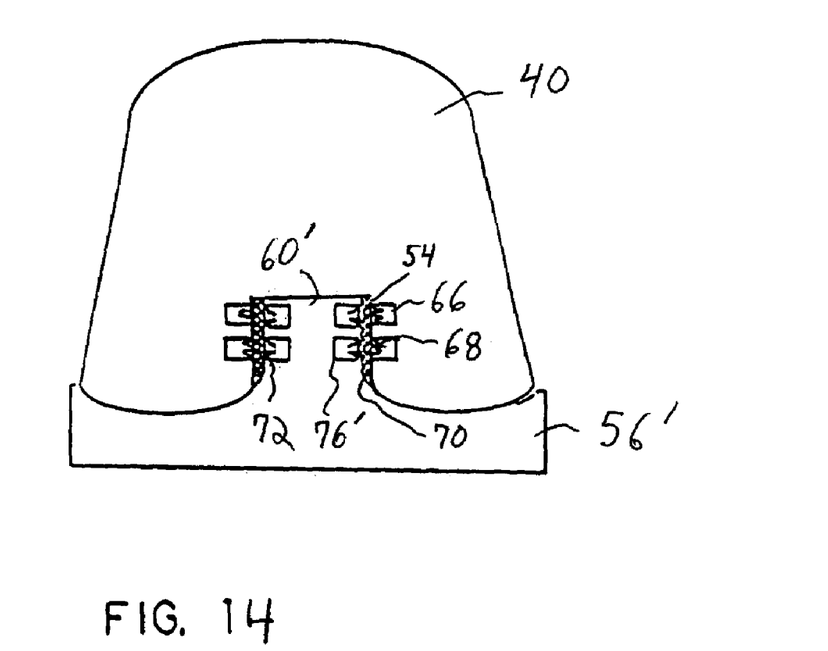
FIG. 14 is a frontal view showing the interaction between the tibial component and the femoral component concurrently having the exemplary embodiment of FIG. 6 mounted to the femoral prosthesis component and the exemplary embodiment of FIG. 12 mounted to the tibial prosthesis component.

Consulting FIG. 12, an exploded view of another exemplary embodiment illustrates an example of biologic and/or a biologically reabsorbable inserts 70 for attachment to the sides of the post 60' facing the sides of the intercondylar channel 46'. The inserts 70 may be mounted to prosthetic knee components to provide a biologically reabsorbable liner or cap 54, 64 as discussed above. This will at least temporarily reduce the periarticular tolerance between components, particularly tibial and femoral, so as to reduce the periarticular instability before the patient's body can compensate. These inserts 70 include a layer 74 of biologically reabsorbable material having male tabs 72 of biologically reabsorbable material that extend therefrom. The post 60' of the present exemplary embodiment includes corresponding female recesses 76' adapted to receive the tabs 72 and thus mount the inserts 70 thereto in a snap-fit manner. FIG. 13 shows the assembled embodiment of FIG. 12. FIG. 14 shows the embodiment of the tibial component 56' and associated inserts 70 of FIG. 12 combined with the embodiment of the femoral component 40 and associated liners 54 shown and described in FIG. 6.

In the above exemplary embodiments, the liners 54, 64 and inserts 70 may advantageously be absorbed over a relatively short period (i.e., several weeks or months) and be replaced by tissue (such as scar tissue) that provides for long-term knee stability and, hopefully, normal range of motion. It is also within the scope of the invention that the liner materials be absorbed over a longer or shorter time span or not be appreciably absorbed at all. Such selection of materials will depend upon the application.

Examples of biologic materials for use with the liners 54, 64 and inserts 70 include, without limitation, extra cellular matrices (ECMs). Examples of ECMs include, without limitation, porcine small intestine submucosa (SIS), xenogeneic small intestine submucosa (xSIS), urinary bladder submucosa (UBS), laminated intestinal submucosa, glutaraldehyde-treated bovine pericardium (GLBP). The biologic materials may be layered, molded, formed, braided, perforated, multilaminated, grafted or otherwise manipulated to achieve the desired properties and dimensions associated with the liners 54, 64 and inserts 70.

Examples of biologically reabsorbable materials for use with the liners 54, 64 and inserts 70 may include, without limitation, MONOCRYL (poliglecaprone 25), PDS II (polydioxanone), surgical gut suture (SGS), gut, coated VICRYL (polyglactin 910, polyglactin 910 braided), human autograft tendon material, collagen fiber, POLYSORB, poly-L-lactic acid (PLLA), polylactic acid (PLA), polylactides (Pla), racemic form of polylactide (D,L-Pla), poly(L-lactide-co-D, L-lactide), 70/30 poly(L-lactide-co-D,L-lactide), polyglycolides (PGa), polyglycolic acid (PGA), polycaprolactone (PCL), polydioxanone (PDS), polyhydroxyacids, and resorbable plate material (see e.g. Orthopedics, October 2002, Vol. 25, No. 10/Supp.). The biologically reabsorbable materials may be layered, molded, formed, braided, perforated, multilaminated, grafted or otherwise manipulated to achieve the desired properties and dimensions associated with the liners 54, 64 and inserts 70. For example, the MONOCRYL (poliglecaprone 25), PDS II (polydioxanone), and resorbable plate materials may be block formed, while the surgical gut suture (SGS), gut, coated VICRYL (polyglactin 910), human autograft tendon material, collagen fiber, POLYSORB, poly-L-lactic acid (PLLA), polylactic acid (PLA), polyglycolic acid, and porcine small intestinal submucosa (SIS) material may be layered and formed. It is within the scope and spirit of the present invention that any of the above materials and techniques may be used individually, alternatively, or in conjunction to produce the liners 54, 64 or inserts 70.

Exemplary materials comprising the biologically reabsorbable fasteners 68, 72 include, without limitation, poly-L-lactic acid (PLLA) and collagen. As will be apparent to those of ordinary skill in the art, there are many other biologic and/or biologically reabsorbable materials that can be used for the liners 54, 64, inserts 70, or fasteners 68, 72, all of which and others developed hereafter shall fall within the scope of the invention.

It is also within the scope of the present invention to "load" (disburse, coat, impregnate, etc.) the biologic and/or biologically reabsorbable materials comprising the liners 54, 64 or inserts 70 with agents that could hasten or assist in tissue development, assist in clotting, and/or fight infection. Exemplary agents may include, for example, without limitation, concentrated platelets (SYMPHONY from Depuy Orthapedic) and gentamicin.

With each of the above embodiments, it is within the scope of the invention to incorporate growth stimulating factors with the biologic or biologically reabsorbable materials. Examples of such growth stimulating factors include, without limitation, growth factor beta (GFB-$\beta$), basic fibroblast growth factor (bFGF), fibroblast growth factor (FGF), epidermal growth factor (EFG), transforming growth factor-$\beta$1 (TGF-$\beta$1), vascular endothelial growth factor (VEGF), connective tissue growth factor (CTGF), platelet-derived growth factor (PDGF), direct-mediated gene transfer, fibroblast-mediated gene transfer, myoblast-mediated gene transfer, TGF-$\beta$ gene family, adenovirus-mediated gene transfer, recombinant adenovirus-induced tendon adhesion formation, BMP-12, bone morphogenetic protein-2 gene transfer, growth and differentiation factor-5 (GDF-5) and, insulin like growth factor (IFG). (See e.g. Koski et al., "Tissue-Engineered Ligament—Cells, Matrix, and Growth Factors", July 2000 Tissue Engineering in Orthopedic Surgery, Volume 31, No. 3), (see e.g., Boyer, "Using Growth Factors to Enhance Tendon and Ligament Repair", Orthopaedic Research Society Symposia, AAOS Annual Meeting New Orleans February 2003). Several of these growth factors have been proposed as possible mitogens in fibroblast growth.

It is also within the scope of the invention to incorporate connective tissue stem cells and progenitors with the biologic or biologically reabsorbable materials disclosed in the above embodiments. These connective tissue stem cells and progenitors may be incorporated into the liners 54, 64 and inserts 70 to provide a three dimensional framework for the creation of engineered tissue for, in an exemplary application, {What are some exemplary applications???}. Examples of such connective tissue stem cells and progenitors include, without limitation, fibroblastic colony-forming cells, fibroplast colony-forming units (CFU-F), bone marrow stromal cells, mesenchymal stem cells (MSC), and vascular pericytes. (See e.g. Meschler et al. "Connective Tissue Progenitors: Practical Concepts for Clinical Applications", 2002 Clinical Orthopaedics and Related Research, No. 395, pp. 66-80).

It is also within the scope of the invention to incorporate hematopoietic stem cells and progenitors with the biologic or biologically reabsorbable materials disclosed in the above embodiments. These hematopoietic stem cells and progenitors may be incorporated into the liners 54, 64 and inserts 70 to provide any cell making up circulating blood and the immune system for, in an exemplary application, inhibiting infection after surgery.

It is additionally within the scope and spirit of the present invention to provide a biologic and/or a biologically reabsorbable liner 54, 64 or insert 70 manipulatable to varying dimensions before and during surgery to better accommodate the patient's unique biomechanics and size of the prostheses. An exemplary liner 54, 64 and insert 70 might be manipulatable by mounting thereto a second biologic and/or biologically reabsorbable insert or attachment or an exemplary liner may be reduced by cutting or shaving material therefrom. Likewise, it is within the scope and spirit of the present invention to allow a physician to manipulate the dimensions and locations of fasteners utilized to secure the biologic and/or a biologically reabsorbable liner 54, 64 or insert 70 to any of the above structural components.

It is also within the scope and spirit of the present invention to provide biologic and/or biologically reabsorbable liners, caps or inserts in other locations of a prosthetic knee or another prosthetic joint implant to provide temporary stability to the joint before the patient's natural tissue is prepared to assume such a role.

Following from the above description and invention summaries, it should be apparent to those of ordinary skill in the art that, while the apparatuses and methods herein described constitute exemplary embodiments of the present invention, it is to be understood that the inventions contained herein are not limited to these precise embodiments and that changes may be made to them without departing from the scope of the inventions as defined by the claims. Additionally, it is to be understood that the invention is defined by the claims and it not intended that any limitations or elements describing the exemplary embodiments set forth herein are to be incorporated into the meanings of the claims unless such limitations or elements are explicitly listed in the claims. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A knee prosthesis comprising:
    a tibial component to be mounted to a patient's tibia;
    a femoral component to be mounted to a patient's femur, and to be pivotally coupled to the tibial component to form a prosthetic knee joint; and
    a lining mounted to at least one of the tibial component and the femoral component in the prosthetic knee joint, and remote from native connective tissue, so that the lining is between the tibial component and the femoral component within a prosthetic intercondylar channel of the femoral component to supplement periarticular stability between the tibial component and the femoral component; and
    the lining comprising a biologically reabsorbable lining material whereby degradation of the lining does not appreciably hinder the functionality of the femoral component and the tibial component.

2. The knee prosthesis of claim 1, further comprising at least one fastener for mounting the lining to one of the tibial component and the femoral component, wherein the fasteners comprise a biologically reabsorbable fastener material.

3. The knee prosthesis of claim 2, wherein the fastener material includes at least one, or an equivalent, of:
    a poly-L-lactic acid material; and
    collagen.

4. The knee prosthesis of claim 2, wherein the fasteners are taken from a group consisting of:
    screws;
    snaps;
    clips;
    keyways; and
    rivets.

5. The knee prosthesis of claim 1, wherein the lining material includes at least one, or an equivalent, of:
    extra cellular matrices (ECMs);
    poliglecaprone 25;
    polydioxanone
    surgical gut suture (SGS);
    gut;
    polyglactin 910;
    human autograft tendon material;
    collagen fiber;
    poly-L-lactic acid (PLLA);
    polylactic acid (PLA);
    polylactides (Pla);
    racemic form of polylactide (D,L-Pla);
    poly(L-lactide-co-D,L-lactide);
    polyglycolides (PGa);
    polyglycolic acid (PGA);
    polycaprolactone (PCL);
    polydioxanone (PDS);
    polyhydroxyacids; and
    resorbable plate material.

6. The knee prosthesis of claim 5, wherein the extra cellular matrices (ECMs) includes at least one, or an equivalent, of:
    porcine small intestine submucosa (SIS);
    xenogeneic small intestine submucosa (xSIS);
    urinary bladder submucosa (UBS);
    laminated intestinal submucosa; and
    glutaraldehyde-treated bovine pericardium (GLBP).

7. The knee prosthesis of claim 1, wherein the lining material is to be substantially absorbed and replaced by the patient's tissue within approximately 6 months after implantation.

8. The knee prosthesis of claim 1, wherein at least one surface of the lining approximates a contour of a surface of at least one of the tibial component and the femoral component to which the lining is mounted.

9. The knee prosthesis of claim 1, wherein at least a portion of the lining is conforming to the topography of at least one of the tibial component and the femoral component to which the lining is mounted.

10. The knee prosthesis of claim 1, wherein the lining is mounted to the tibial component and includes an outer surface that approximates a contour of a surface of the femoral component most likely coming into contact therewith.

11. The knee prosthesis of claim 10, wherein the contour of an outer surface of the femoral component approximates an inner surface of at least one of a prosthetic medial condyle element and a prosthetic lateral condyle element partially defining the prosthetic intercondylar channel.

12. The knee prosthesis of claim 1, wherein the lining is mounted to the femoral component and includes an outer surface that approximates a contour of a surface of the tibial component passing into the prosthetic intercondylar channel.

13. The knee prosthesis of claim 1, wherein the lining material is loaded with at least one of a tissue promotion agent, a clotting agent and an antibiotic agent.

14. The knee prosthesis of claim 13, wherein the lining material is loaded with a clotting agent that includes concentrated platelets.

15. The knee prosthesis of claim 13, wherein the lining material is loaded with an antibiotic agent that includes gentamicin.

16. The knee prosthesis of claim 1, wherein:
the tibial component includes a stabilizing post at its proximal end to be received within the intercondylar channel of the femoral component; and
the lining is mounted to at least one of the stabilizing post and a surface of the intercondylar channel.

17. The knee prosthesis of claim 1, wherein the lining material is loaded with at least one of connective tissue stem cells and connective tissue stem cell progenitors.

18. The knee prosthesis of claim 17, wherein the connective tissue stem cells and connective tissue stem progenitors are taken from the group consisting of:
fibroblastic colony-forming cells, fibroplast colony-forming units (CFU-F), bone marrow stromal cells, mesenchymal stem cells (MSC), and vascular pericytes.

19. The knee prosthesis of claim 1, wherein the lining material is loaded with a growth stimulating factor.

20. The knee prosthesis of claim 19, wherein the growth stimulating factor is taken from the group consisting of: growth factor beta (GFB-β), basic fibroblast growth factor (bFGF), fibroblast growth factor (FGF), epidermal growth factor (EFG), transforming growth factor-β1 (TGF-β1), vascular endothelial growth factor (VEGF), connective tissue growth factor (CTGF), platelet-derived growth factor (PDGF), direct-mediated gene transfer, fibroblast-mediated gene transfer, myoblast-mediated gene transfer,TGF-β gene family, adenovirus-mediated gene transfer, recombinant adenovirus-induced tendon adhesion formation, BMP-12, bone morphogenetic protein-2 gene transfer, growth and differentiation factor-5 (GDF-5), and insulin like growth factor (IFG).

21. The knee prosthesis of claim 1, wherein the lining material is loaded with at least one of hematopoietic stem cells and hematopoietic stem cells progenitors.

22. A knee prosthesis comprising:
a femoral component to be mounted to a patient's femur;
a tibial component to be mounted to the patient's tibia, the tibial component including a stabilizing post at its proximal end to be received within a prosthetic intercondylar channel of the femoral component to form a prosthetic hinge-type joint coupling; and
a lining mounted to at least one of the stabilizing post and an articulating surface of the femoral component, the articulating surface of the femoral component at least partially defining the prosthetic intercondylar channel, so as to at least temporarily, supplement periarticular stability between the stabilizing post and the prosthetic intercondylar channel;
the lining comprising a biologically reabsorbable lining material whereby degradation of the lining does not appreciably hinder the functionality of the femoral component and the tibial component.

23. The knee prosthesis of claim 22, further comprising at least one fastener for mounting the lining to at least one of the stabilizing post of the tibial component and the articulating surface of the femoral component, the articulating surface of the femoral component at least partially defining the prosthetic intercondylar channel, wherein the fastener comprises a biologically reabsorbable fastener material.

24. The knee prosthesis of claim 22, wherein the lining material includes at least one, or an equivalent, of:
extra cellular matrices (ECMs);
poliglecaprone 25;
polydioxanone;
surgical gut suture (SGS);
gut;
polyglactin 910;
human autograft tendon material;
collagen fiber;
poly-L-lactic acid (PLLA);
polylactic acid (PLA);
polylactides (Pla);
racemic form of polylactide (D,L-Pla);
poly(L-lactide-co-D,L-lactide);
polyglycolides (PGa);
polyglycolic acid (PGA);
polycaprolactone (PCL);
polydioxanone (PDS);
polyhydroxyacids; and
resorbable plate material.

25. The knee prosthesis of claim 24, wherein the extra cellular matrices (ECMs) includes at least one of:
porcine small intestine submucosa (SIS);
xenogeneic small intestine submucosa (xSIS);
urinary bladder submucosa (UBS);
laminated intestinal submucosa; and
glutaraldehyde-treated bovine pericardium (GLBP).

26. The knee prosthesis of claim 22, wherein the lining material is to be substantially absorbed by a patient's body after implantation and to be substantially replaced by the patient's tissue.

27. The knee prosthesis of claim 26, wherein the lining material is to be substantially absorbed and replaced by the patient's tissue within approximately 6 months after implantation.

28. The knee prosthesis of claim 22, wherein the lining material is loaded with at least one of a tissue promotion agent, a clotting agent, and an antibiotic agent.

29. The knee prosthesis of claim 28, wherein the lining material is loaded with a clotting agent tat includes concentrated platelets.

30. The knee prosthesis of claim 28, wherein the lining material is loaded with an antibiotic agent that includes gentamicin.

31. The knee prosthesis of claim 22, wherein the lining material is loaded with at least one of connective tissue stem cells and connective tissue stem cell progenitors.

32. The knee prosthesis of claim 31, wherein the connective tissue stem cells and connective tissue stem progenitors are taken from the group consisting of:
fibroblastic colony-forming cells, fibroplast colony-forming units (CFU-F), bone marrow stromal cells, mesenchymal stem cells (MSC), and vascular pericytes.

33. The knee prosthesis of claim 22, wherein the lining material is loaded with a growth stimulating factor.

34. The knee prosthesis of claim 33, wherein the growth stimulating factor is taken from the group consisting of: growth factor beta (GFB-β), basic fibroblast growth factor (bFGF), fibroblast growth factor (FGF), epidermal growth factor (EFG), transforming growth factor-β1 (TGF-β1), vascular endothelial growth factor (VEGF), connective tissue growth factor (CTGF), platelet-derived growth factor (PDGF), direct-mediated gene transfer, fibroblast-mediated gene transfer, myoblast-mediated gene transfer,TGF-β gene family, adenovirus-mediated gene transfer, recombinant adenovirus-induced tendon adhesion formation, BMP-12, bone morphogenetic protein-2 gene transfer, growth and differentiation factor-5 (GDF-5), and insulin like growth factor (IFG).

35. The knee prosthesis of claim 22, wherein the lining material is loaded with at least one of hematopoietic stem cells and hematopoietic stem cells progenitors.

36. A knee prosthesis comprising:
 a tibial component to be mounted to a patient's tibia;
 a femoral component to be mounted to a patient's femur, and to be pivotally coupled to the tibial component to form a prosthetic knee joint; and
 a biologically reabsorbable lining being selectively attachable to at least one of the tibial component and the femoral component in the prosthetic knee joint so that the lining is mounted between the tibial component and the femoral component within a prosthetic intercondylar channel of the femoral component to supplement periarticular stability between the tibial component and the femoral component, whereby degradation of the lining does not appreciably hinder the functionality of the femoral component and the tibial component.

\* \* \* \* \*